(12) United States Patent
Andres et al.

(10) Patent No.: US 7,493,812 B2
(45) Date of Patent: Feb. 24, 2009

(54) ISOMETRIC STRENGTH TESTING APPARATUS

(75) Inventors: Patricia Lee Andres, Reading, MA (US); Mark Kleiman, Framingham, MA (US); Michael Barenboym, Framingham, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 11/715,200

(22) Filed: Mar. 7, 2007

(65) Prior Publication Data

US 2008/0216570 A1 Sep. 11, 2008

(51) Int. Cl.
*A61B 5/22* (2006.01)
(52) U.S. Cl. .................................................. 73/379.01
(58) Field of Classification Search .............. 73/379.01, 73/379.02; 600/587; 482/8
See application file for complete search history.

(56) References Cited

U.S. PATENT DOCUMENTS

| | | | |
|---|---|---|---|
| 3,285,070 A | 11/1966 | McDonough |
| 3,374,675 A | 3/1968 | Keropian |
| 3,397,884 A | 8/1968 | Blasi |
| 3,752,144 A | 8/1973 | Weigle, Jr. |
| 4,236,528 A | 12/1980 | Stanec et al. |
| 4,333,340 A | 6/1982 | Elmeskog |
| 4,501,148 A | 2/1985 | Nicholas et al. |
| 4,702,108 A | 10/1987 | Amundsen et al. |
| 4,733,859 A | 3/1988 | Kock et al. |
| 4,742,832 A | 5/1988 | Kauffmann et al. |
| 4,882,677 A | 11/1989 | Curran |
| 4,883,066 A | 11/1989 | Widdoes et al. |
| 4,939,933 A | 7/1990 | Curran |
| 4,972,711 A | 11/1990 | Jain et al. |
| 5,244,441 A | 9/1993 | Dempster et al. |
| 5,269,738 A | 12/1993 | Boren |
| 5,275,045 A | 1/1994 | Johnston et al. |
| 5,302,164 A | 4/1994 | Austin |
| 5,335,649 A | 8/1994 | Randall et al. |
| 5,447,356 A | 9/1995 | Snijders |

(Continued)

FOREIGN PATENT DOCUMENTS

DE 2004002975 5/2004

(Continued)

OTHER PUBLICATIONS

International Search Report and Written Opinion from corresponding PCT application No. US2008/002911. Jul. 24, 2008.

(Continued)

*Primary Examiner*—Jewel Thompson
(74) *Attorney, Agent, or Firm*—Wolf, Greenfield & Sacks, P.C.

(57) ABSTRACT

An isometric strength testing device includes a base for selectively supporting either a chair or a wheelchair for the subject to be tested. A pair of limb supports are positioned on the base, one to immobilize an arm and the other a leg of the subject. Each support includes a band carrying a load cell for generating a signal measurement of the force applied to the cell. Goniometers are associated with the supports for establishing appropriate angles of the subject's limbs at the knee and elbow. A computer connected to the force plates processes and displays data generated by the load cells.

19 Claims, 9 Drawing Sheets

U.S. PATENT DOCUMENTS

| | | | |
|---|---|---|---|
| 5,800,310 A | 9/1998 | Jones | |
| 6,149,550 A | 11/2000 | Shteingold | |
| 6,227,047 B1 | 5/2001 | Livingston | |
| 6,228,000 B1 | 5/2001 | Jones | |
| 6,325,767 B1 | 12/2001 | Wolff et al. | |
| 6,478,529 B1 | 11/2002 | Willey et al. | |
| 6,595,901 B2 | 7/2003 | Reinbold et al. | |
| 6,706,003 B2 | 3/2004 | Perrad et al. | |
| 6,716,143 B1 | 4/2004 | Martin | |
| 6,770,013 B2 | 8/2004 | Stillinger | |

FOREIGN PATENT DOCUMENTS

| | | |
|---|---|---|
| JP | 11-290301 | 10/1999 |
| JP | 03-000574 | 1/2003 |
| JP | 05-013483 | 1/2005 |
| JP | 05-211420 | 8/2005 |
| WO | WO 90/11049 | 10/1990 |

OTHER PUBLICATIONS

Medical Engineering & Physics "Measurement of isometric muscle strength" Apr. 11, 2000, pp. 167-174.

Applied Ergonomics "Three-dimensional computerized isometric strength measurement system" May 8, 2006, pp. 285-292.

Ezkerra, Jose et al. "Automatized robotic system for isometric muscle strength measurement in humans" Oct. 29, 1992, pp. 1437-1439.

ISOMETRIC STRENGTH TESTING APPARATUS

BACKGROUND OF INVENTION

1. Field of Invention

This invention relates to isometric strength testing apparatus and method, and more particularly relates to isometric strength testing for measuring disease progression in ALS patients.

2. Background

In the past decade, the number of candidate therapeutic agents for the treatment of ALS has greatly increased, and the ability of the clinical trial community to test these agents is limited due to cost, time, and especially resource constraints. Muscle strength is an important determinant of function in ALS and thus is a valuable outcome measure in clinical trials. Establishing a disease progression rate for each individual provides an extremely accurate method to determine even modest therapeutic effects. The equipment heretofore available to perform such tests is expensive and/or requires a highly trained evaluator.

Sample size determination is largely dependent on the variance of both the measurement system and the between-subject variation. Therefore, selection of the precise outcome measures is a critically important component of clinical trial design. Because strength loss within each subject is very linear, the variation of loss in a particular patient is very small. However, the differences in disease progression rates can be ten-fold or greater between subjects. By establishing each subject's rate of strength loss and comparing each subject to themselves, the sample size requirements are a fraction of the size needed to compare groups of subjects due to the variance of both the measurement system and the between subject variation employed in clinical trials today. Precise, accurate testing of muscle strength may allow much more efficient outcome measure and enable clinical trials to be significantly shorter, less expensive and require considerably less resources.

In accordance with one ALS testing protocol presently used, strength measurement of 18 muscle groups use maximal voluntary isometric contraction (MVIC). A measurement utilizes a strain gage attached to uprights and the subject pulls against a strap attached to the uprights to measure force output of several muscles in the arms and legs. However, this protocol is time intensive, requires the subject to be moved onto a treatment table and undergo multiple position changes during the testing procedure. The equipment used is large consuming substantial floor space, is very difficult to relocate and the cost of the equipment is substantial. Moreover, the testing protocol requires a highly trained evaluator. Furthermore, many subjects discontinue testing due to the difficulty with transfers and positioning as their disease worsens. As a result, many subjects are not tested in the later stages of the disease.

An alternative method to measure muscle strength uses hand-held dynamometry. This method uses a hand-held force gage to measure the force of the subject's muscular resistance. Holding the force gage in his hand, the evaluator attempts to break the subject's resistance. This method is relatively inexpensive, is portable and can be performed in the sitting position in a short time. However, because the force output is dependent on the evaluator overpowering the subject's strength and because many muscles are tested in an anti-gravity position, there are potentially extraneous factors reflected in the measurement. Moreover, testing positions and stabilization by the evaluator make standardization difficult to achieve.

SUMMARY OF INVENTION

The strength-testing apparatus of the present invention measures, records, and analyzes maximal isometric muscle force readings from various muscle groups in all four limbs. The apparatus includes of a platform carrying a chair for the subject and separate leg and arm restraints along with load cells, a microprocessor and a personal computer. The platform preferably is provided with a ramp to enable a wheelchair to be used when the subject cannot be easily transferred to the chair. Restraints separately stabilize an arm and leg of the subject, load cells engage a wrist and lower leg of the subject, apparatus measures the joint angles of the arm and leg to assure that the limbs are at the appropriate angle, and a single test for each limb will measure strength as a raw score and/or a percent of predicted normal and may also provide a cumulative test report showing disease progression over time and calculate the rate of disease progression over a period of time.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
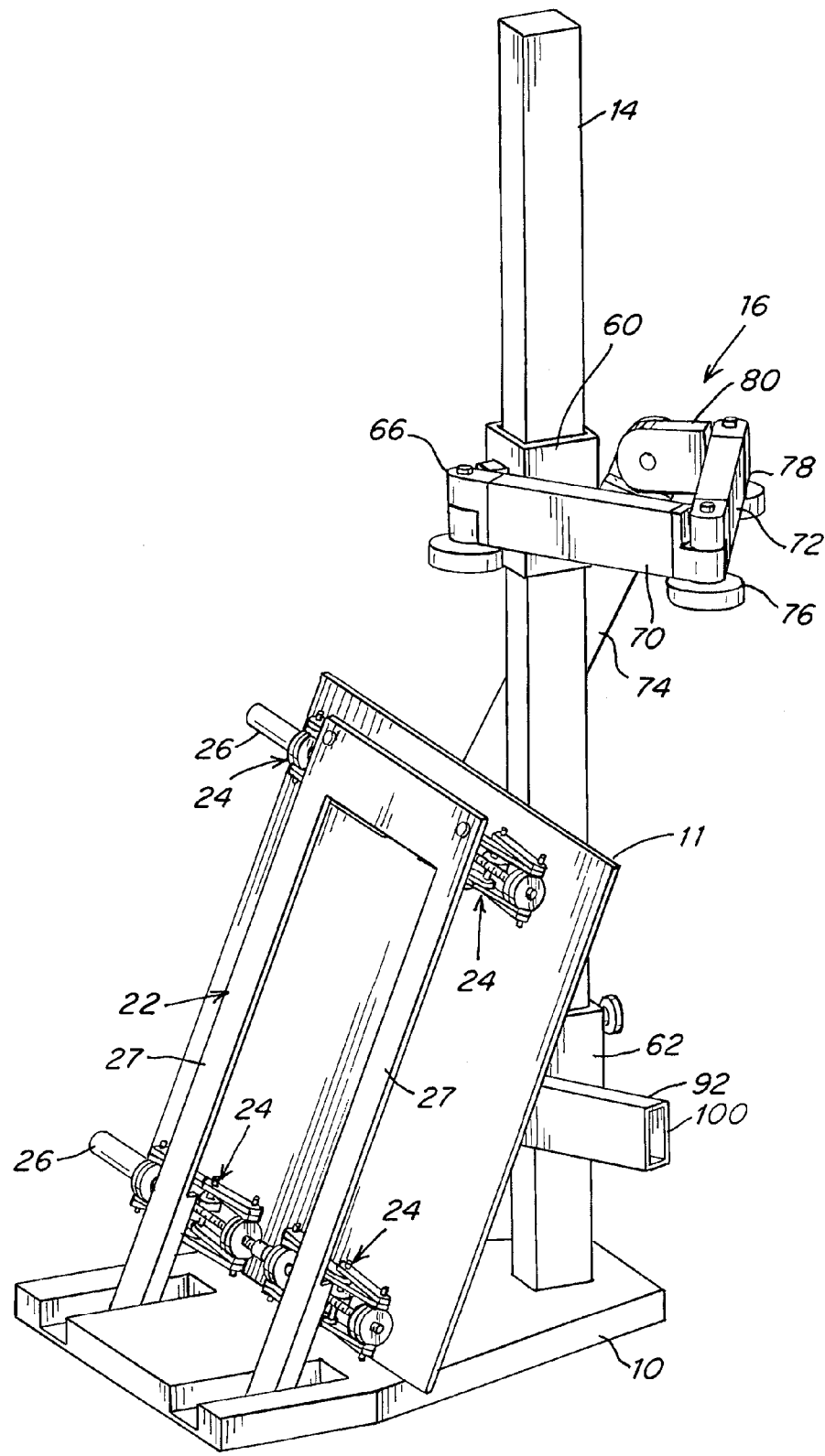
FIG. 1 is a perspective view of many of the major components of the assembled apparatus shown in a collapsed state for storage.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Figure 2:
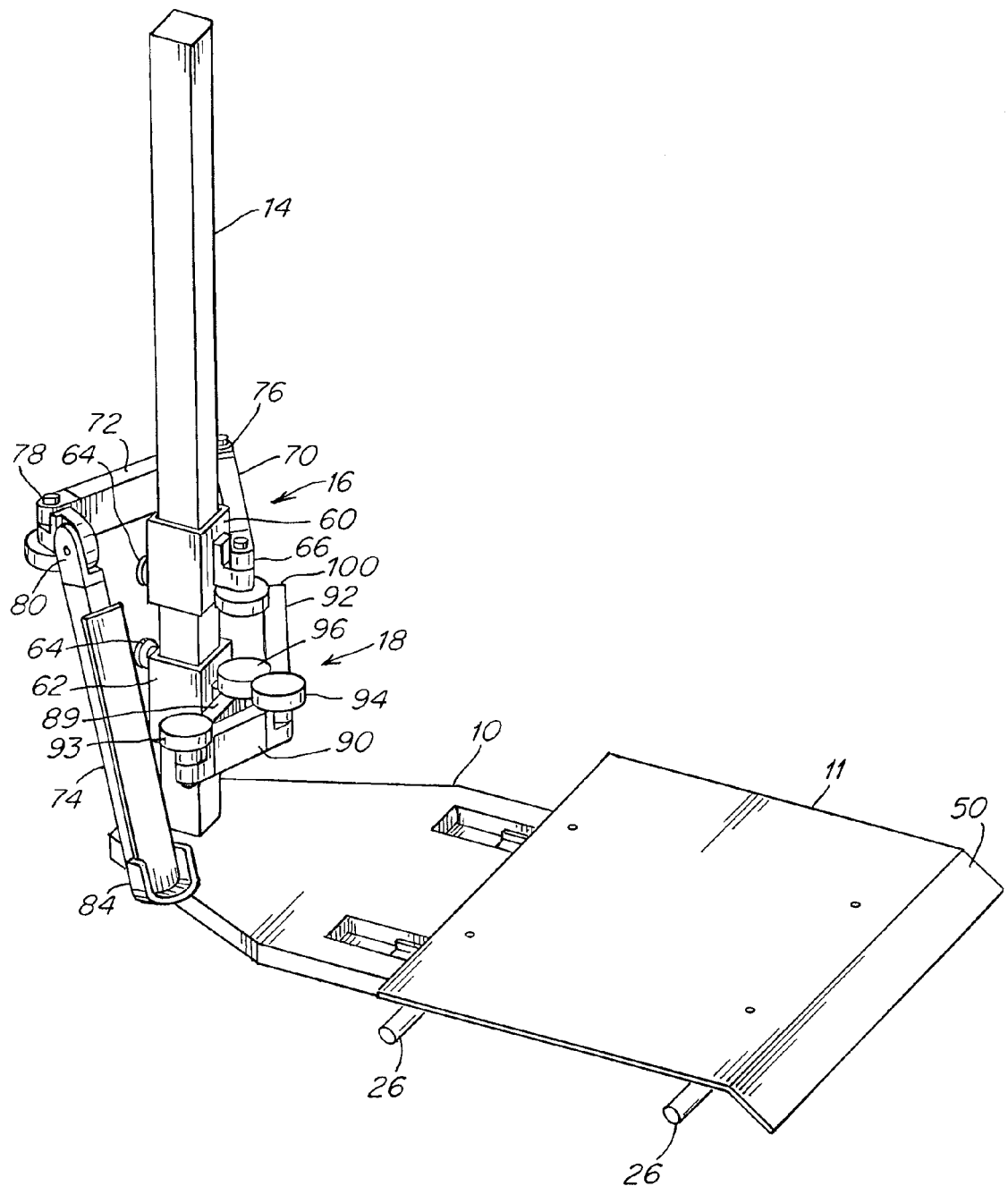
FIG. 2 is a similar view of the apparatus with the base unfolded to the open or useable position.
Figure 3:
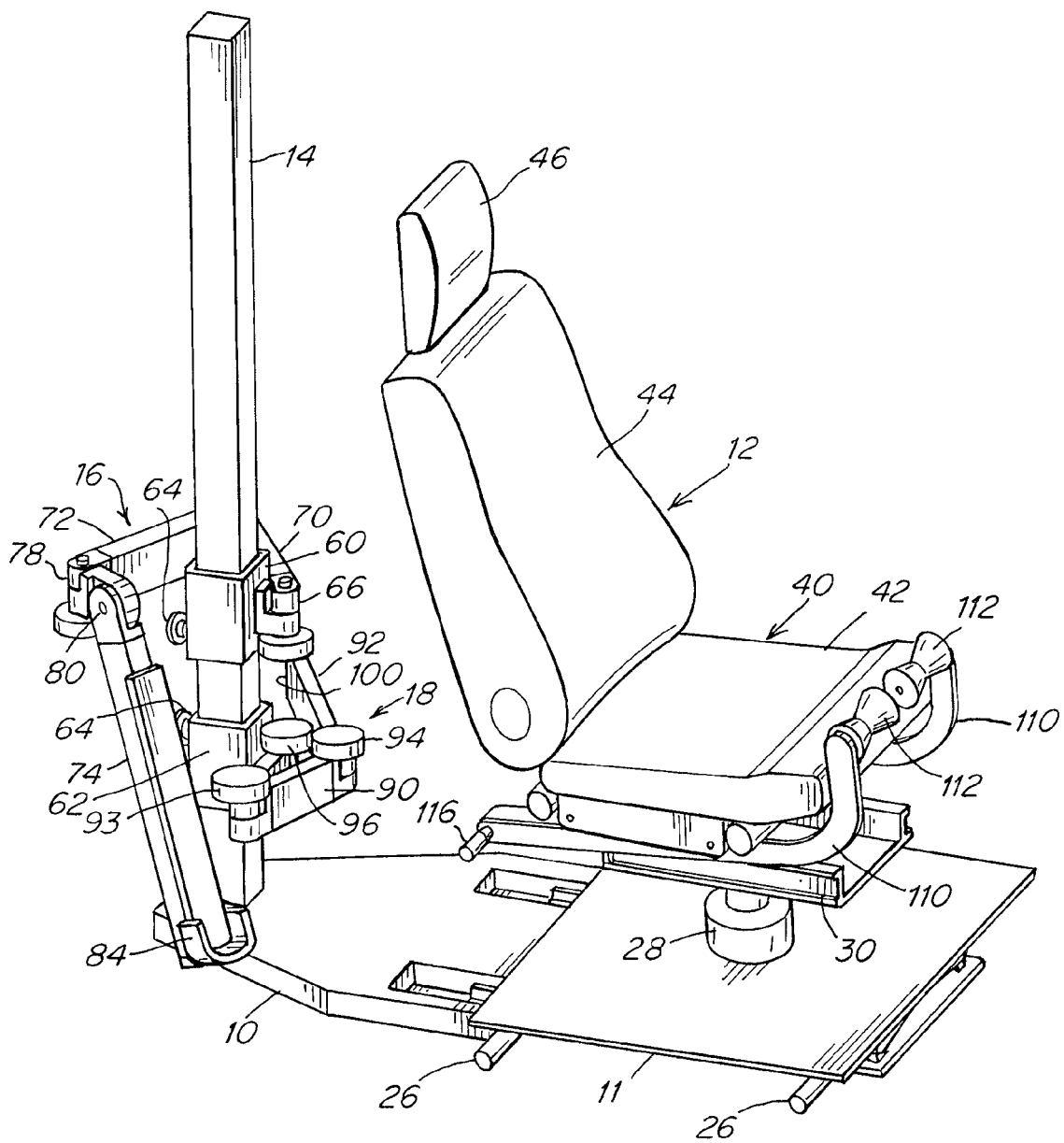
FIG. 3 is a perspective view of the unfolded apparatus with a chair attached and positioned for easy access by a subject.

FIGS. 1-3 show the apparatus folded in stored position and in position to accept a subject to be tested. The strength testing apparatus shown in accordance with one embodiment of the invention includes a base 10 intended to rest on the floor or other surface when the apparatus is in use. The base in turn carries a platform 11 that supports a chair 12 in which the subject sits for testing. The base also carries a column 14 to which a pair of limb supports 16 and 18 are connected. The platform 11 may also be used to support a conventional chair or a wheelchair 12*a* (see FIG. 4) in place of the attached chair 12 as described in detail below.

Figure 5:
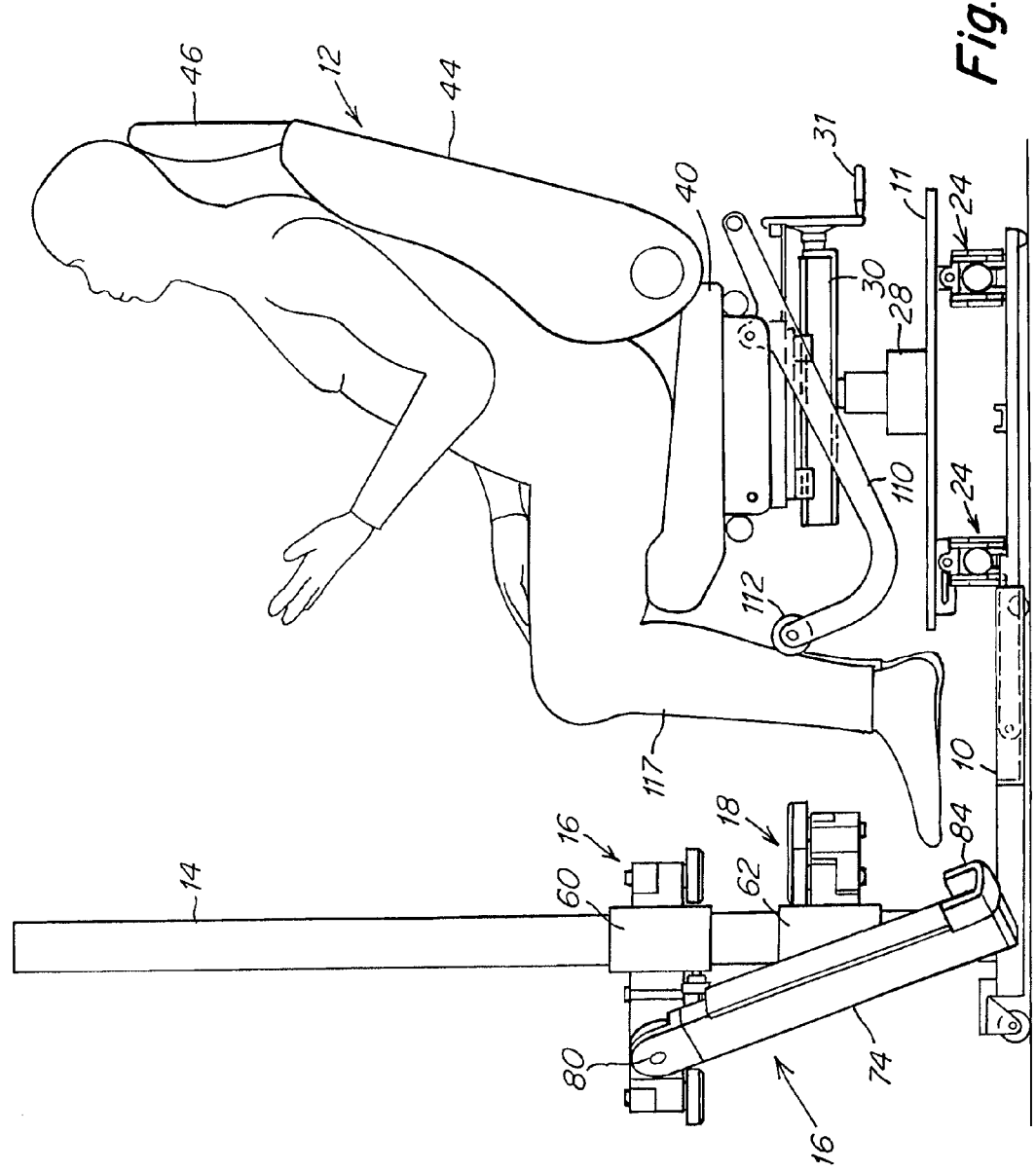
FIG. 5 is a side view of the apparatus of FIG. 3 with the subject to be tested seated in the chair and facing in a direction to be engaged by the limb restraints.
Figure 5A:
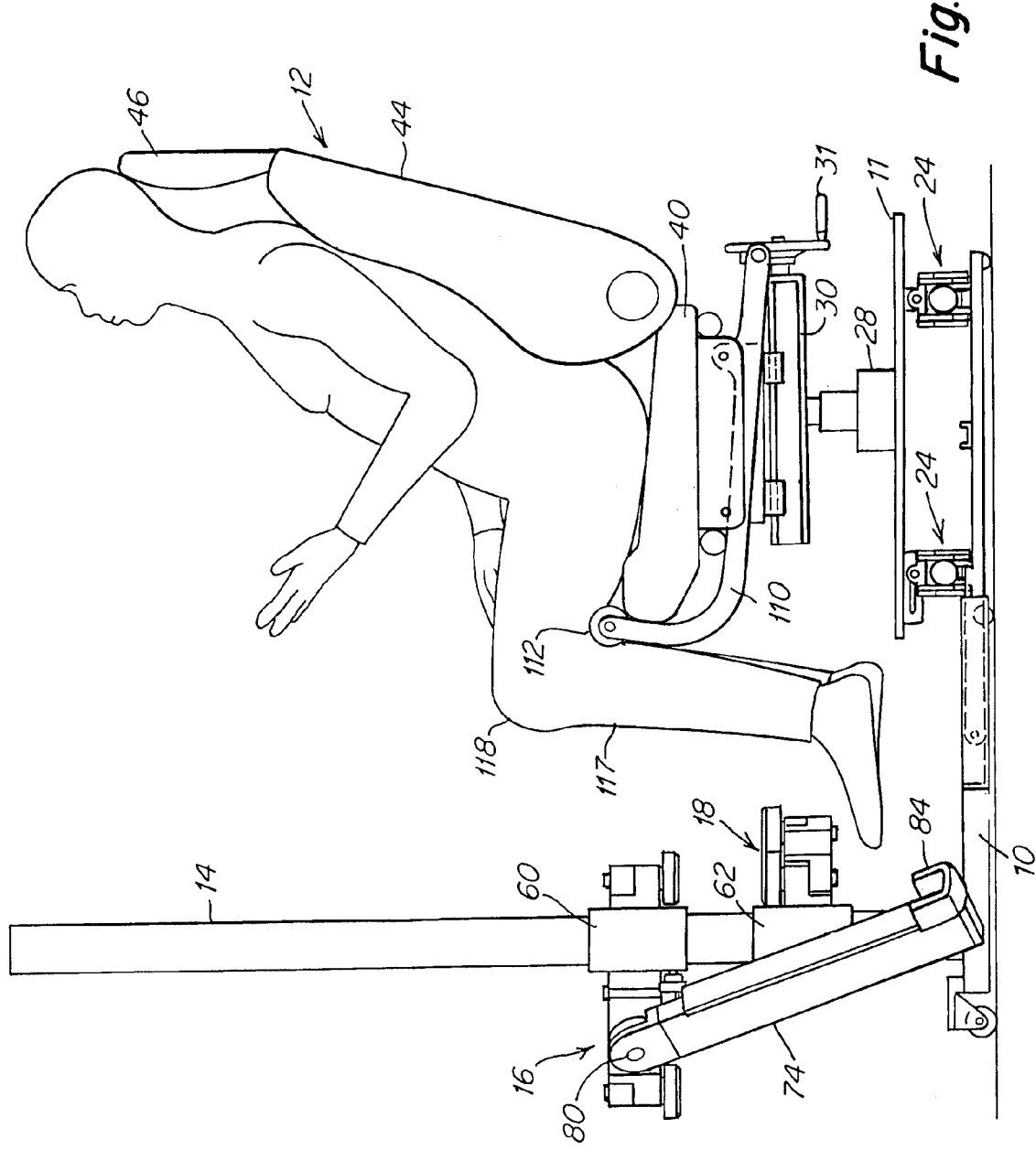
FIG. 5A is a side view similar to FIG. 5 but showing the leg rest in position to support the knees of the subject.

In accordance with one embodiment of the invention, the platform 11 carries an adjustable post 28 that supports the chair 12 and enables the chair to rotate to provide easier access for the subject (compare FIGS. 3 and 5). The position of the chair may also be varied to accommodate subjects of different size particularly when the limb supports 16 and 18 are utilized. In accordance with one embodiment of the present invention, the platform 11 is carried by a U-shaped frame 22 pivotally mounted on the base 10, which enables the platform to be raised to the position shown in FIG. 1 to facilitate storage of the apparatus. For use, the U-shaped frame 22 is pivoted about the connections at the end of the legs 27 that join it to the base 10, placing the platform 11 in the horizontal position of FIG. 2.

The platform 11 in accordance with one embodiment of the invention is mounted on the frame 22 by two pairs of scissor jacks 24 disposed beneath the platform. Each pair of scissor jacks in this embodiment preferably includes a connector 26 that accepts a crank handle or other means to operate the scissor jacks to vary the height of the platform. The scissor jacks 24 may also orient the platform at any desired angle with respect to the horizontal, as described below in connection with the use of the apparatus.

As shown in FIGS. 3 and 5, the platform 11 and post 28 carry an adjusting mechanism 30 that in turn supports the chair 12. The mechanism may be operated by the handle 31. The post 28 enables the adjusting mechanism 30 to be rotated about the post axis so as to change the direction in which the chair faces (see FIGS. 3 and 5), and the adjusting mechanism 30 enables the chair 12 to be moved radially with respect to the post axis, all to accommodate the subject's size when a leg or arm is to be engaged by one of the limb supports 16 or 18 on column 14.

While one specific means of mounting the chair 12 is shown, it should be appreciated that the chair may be mounted in many different ways on the platform and it is most advantageous that when the column mounted chair is used, the chair may be moved with respect to the column 14 so that the subject is comfortable and in the precise position appropriate for the tests to be performed. It is also contemplated that the post 28 may be disconnected from or withdrawn into the platform if a free standing chair or a wheelchair is to be used for the subject.

In accordance with one embodiment of the invention, the chair 12 mounted on the post 28 includes a seat 40 with a seat cushion 42, a backrest 44 and a headrest 46 that preferably is height adjustable by means of a slide connection or some other suitable mechanism for connecting the headrest to the backrest. In accordance with another embodiment of the invention, the angular relationship between the seat 40 and backrest 44 may be varied to provide for the comfort of the subject and to facilitate tests performed separately on the arms and legs (see FIGS. 6-8). The backrest adjustment typically may be accomplished by providing an adjusting mechanism in the frame connecting the backrest to the seat. Such mechanisms are well-known in the furniture and automotive arts.

Figure 4:
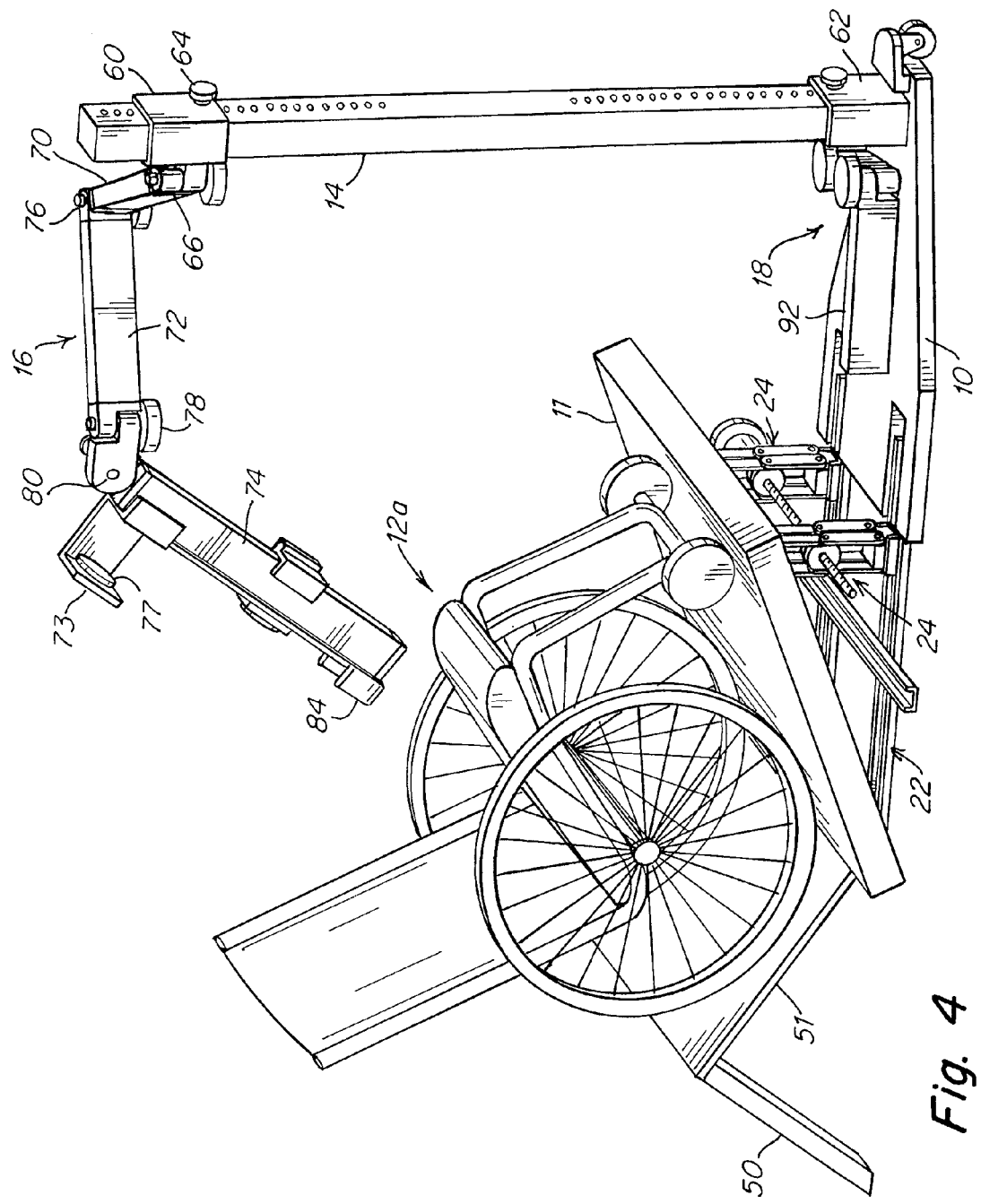
FIG. 4 is a perspective view of the apparatus with the attached chair removed and replaced by a wheelchair.

In accordance with yet another aspect of the invention a ramp 50 may be provided along an edge of the platform 11 (see FIG. 2) to facilitate rolling a wheelchair onto the platform if the subject being tested cannot or should not be seated in the chair 12. If the subject does not require a wheelchair and for some reason chooses not to use the seat 12, the seat 12 may be removed with or without the post 28, and a conventional chair may be used instead. In FIG. 4 a barrier 51 is shown connected to the platform 11 to prevent the wheelchair 12*a* from rolling off it when the platform is tilted to place the wheelchair in an appropriate position for the particular test to be performed. Many different expedients may be used for the same purpose.

Figure 6:
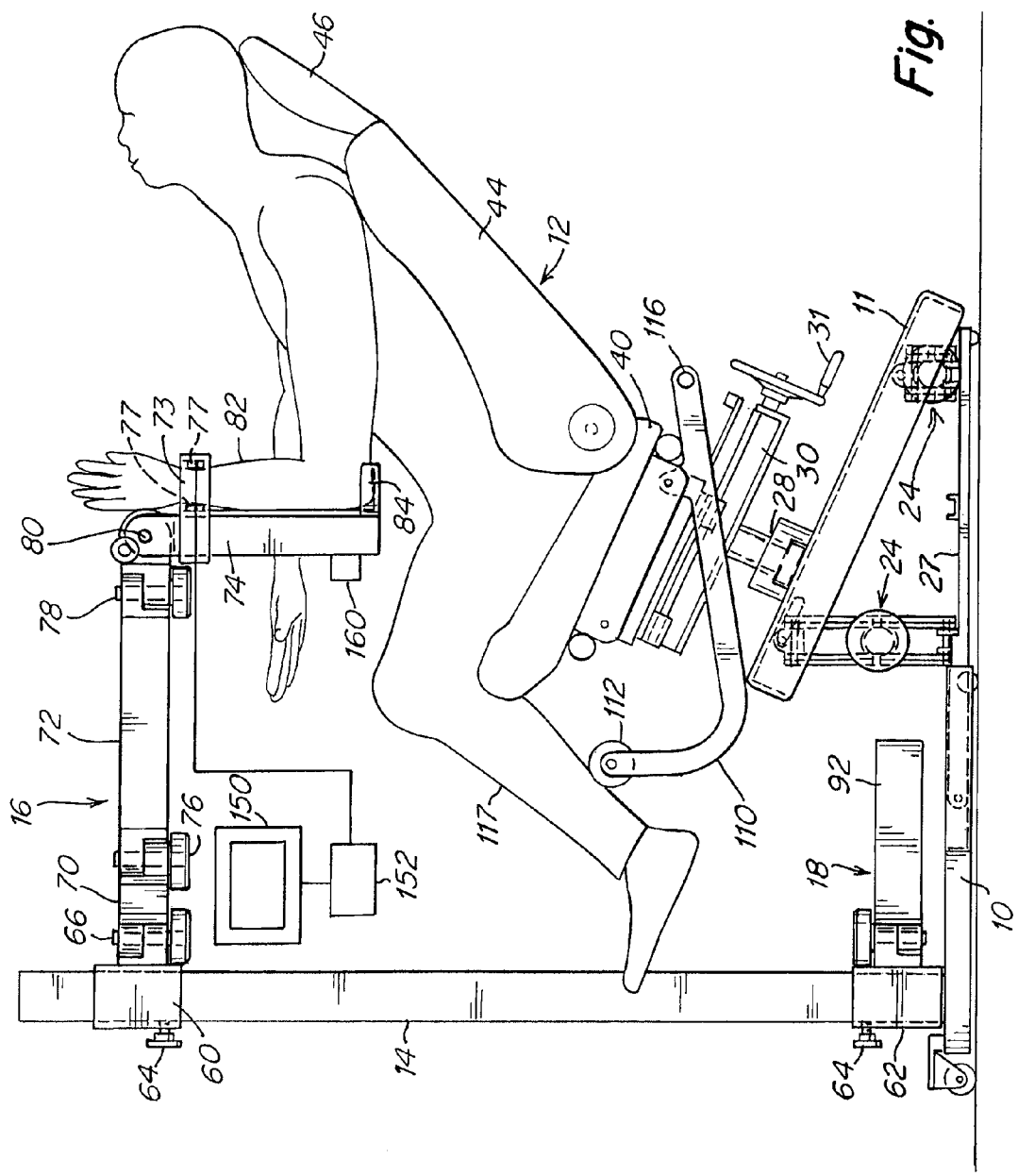
FIG. 6 is a side view of the chair with the arm restraint extended and supporting the left arm of a subject and with the chair tilted.

The limb supports 16 and 18 are each adjustably mounted on the column 14 by means of separate sleeves 60 and 62, each secured in fixed position on the column by means of the set screw type fasteners 64 that extend through a wall of each sleeve and engage the column. Other locking devices such as clamps, cam catches or split blocks may be used as well. The limb support 16 for immobilizing the arm of the subject is joined to the sleeve 60 by a hinge mechanism 66. As shown in FIGS. 3, 4 and 6, in accordance with this embodiment of the invention, the limb support 16 is composed of three sections 70, 72 and 74 connected end-to-end by hinge mechanisms 76, 78 and 80. The end section 74 of the support is designed to directly engage the forearm 82 of the subject and for that purpose a collar 84 is carried on its free end against which the elbow of the subject is positioned when tests are to be performed. The hinges 76, 78 and 80 provide three degrees of freedom so that the section 74 may be positioned to comfortably and separately accommodate the forearm 82 of either arm of the subject seated in any position on the platform with the upper arm and forearm being specifically oriented as prescribed for the tests to be performed. It will be noted that the hinge mechanism 80 provides pivotal motion about a horizontal axis while hinges 66, 76 and 78 provide pivotal motion about vertical axes. This enables arm restraint 16 to restrain either arm of the subject. Height adjustment is also facilitated by the ability to raise and lower the sleeve 60 on column 14.

The mechanism for making the strength measurements may take many different forms, but typically may include load cells carried on the section 74 and appropriate restraints such as a brace or bands that encircle the forearm so as to immobilize the arm. The mechanism may for example include a wrist clamp 73 as shown in FIGS. 4 and 6 that is lightly padded and carries the load cells 77 such as, strain gages, force plates or any other well-known device. Most commonly, the arm section 74 and wrist clamp or other means employed to immobilize the forearm holds the forearm at right angles to the upper arm. It should be appreciated that the limb support 16 may take many different forms, but the illustrated embodiment is the preferred form. Restraints may also be employed engaging the upper arm near the elbow of the subject, and a pad may also be placed under the elbow on the section 74 for the subject's comfort.

The limb support 18, which is specifically intended to immobilize the leg and/or foot, in the embodiment illustrated, is constructed in a fashion similar to that of the limb support 16. As shown in FIGS. 2 and 3, the leg support may include three sections, 89, 90 and 92 hingedly connected end-to-end by hinge mechanisms 93 and 94. The section 89 of the support is connected to the sleeve 62 by hinge mechanism 96. In other embodiments more or fewer sections with a corresponding member of hinge mechanisms may be employed. Height adjustment of the free end 100 of section 92 is afforded by the slidably mounted sleeve 62 on column 14. The hinges 94 and 96 provide adjustment of the position of the end 100 about vertical axes. Although not shown, an additional hinge mechanism like mechanism 80 shown in FIG. 6 may also be incorporated into the limb support 18 to adjust the height of the support. Preferably each hinge mechanism includes or has an associated latching device to enable the leg and arm restraints to be locked in a fixed position as each test is performed.

Figure 7:
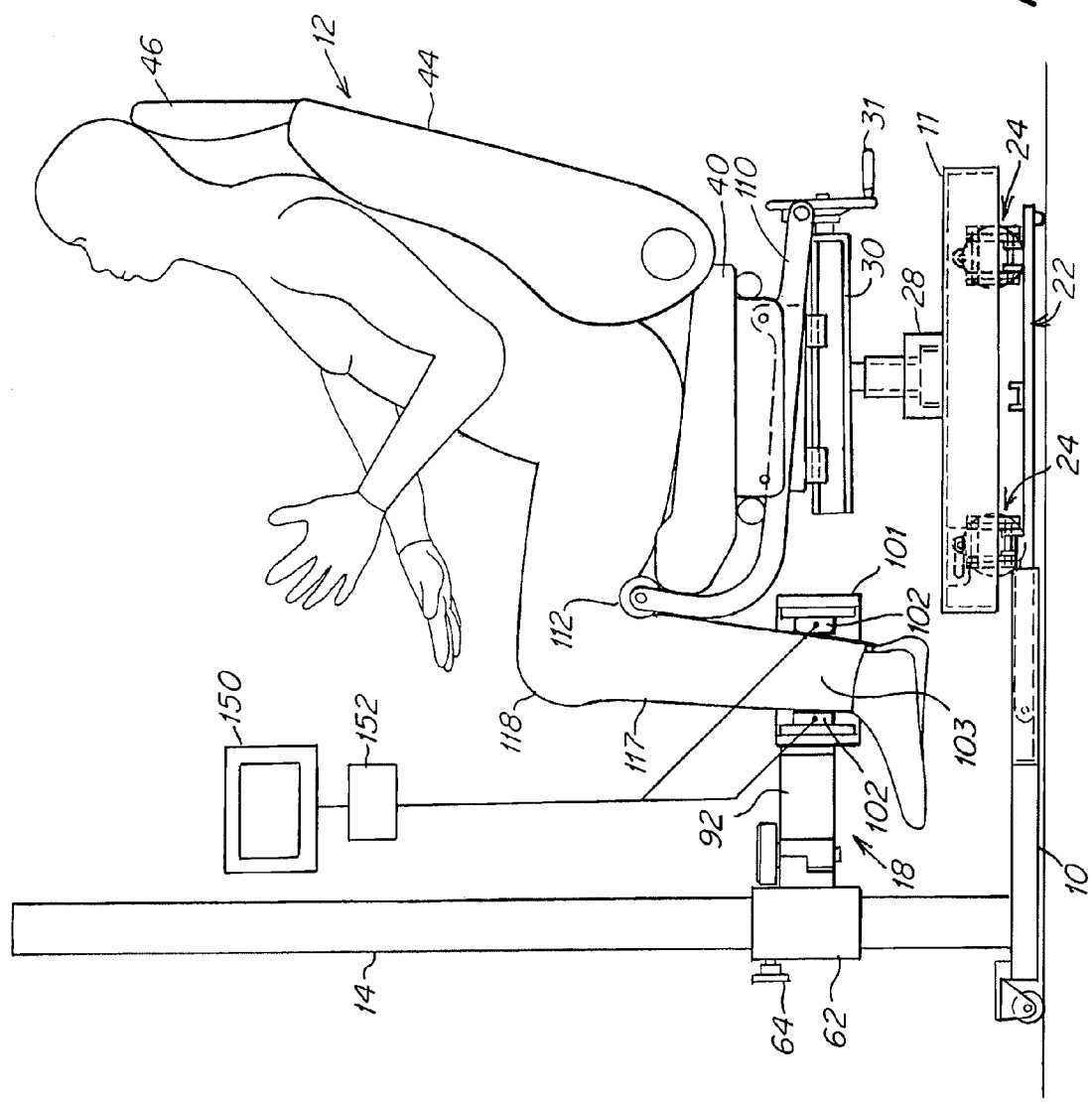
FIG. 7 is a side view similar to FIG. 5A but showing the leg restraints extended and immobilizing the subject's left leg immediately above the ankle.
Figure 8:
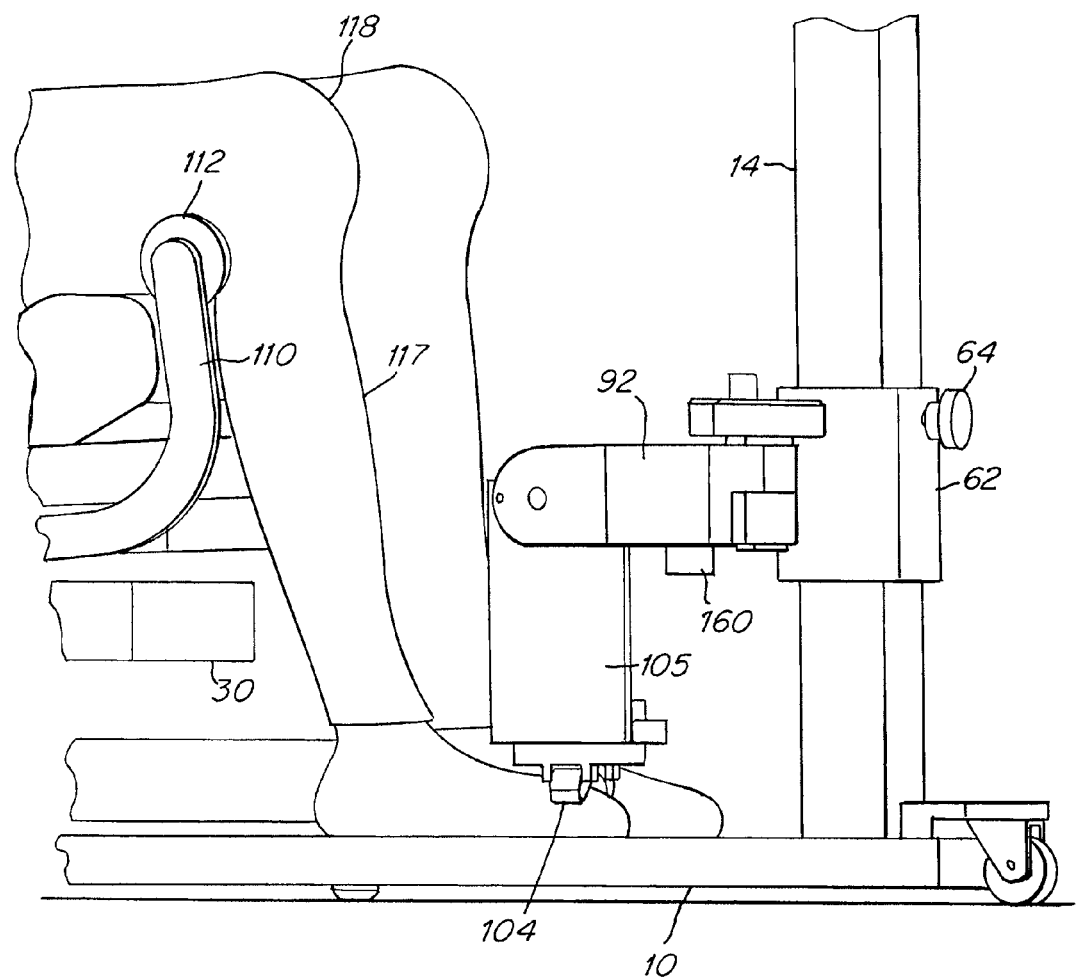
FIG. 8 is a fragmentary perspective view with the subject seated as in FIG. 7 but showing use of the apparatus to measure the force generated by the subject's foot.

In accordance with one embodiment of the invention shown in FIG. 7, the free end of support section 92 carries a collar 101 that engages the ankle 103 of the subject and includes load cells 102 against which the subject will exert extension and flexion forces during performance of the tests. As an alternative test, the subject may place his/her foot beneath a load cell 104 and exert a lifting force against it by trying to bend the ankle upwardly against it. In FIG. 8 the cell 104 is shown held by restraint 105 that opposes the force exerted by the foot. Alternatively, a strap about the forepart of the foot may carry the load cell 104 and restrain the foot.

Additional mechanisms provided by the apparatus to position the legs comprise a pair of braces 110, one mounted on each side of the seat 40 (see FIG. 3). Each brace 110 includes a pad 112 mounted on its forward end and a handle 116 at its back end. The braces are mounted on the support mechanism 30 on each side of the seat 40, and each may separately be moved to several different positions to support the legs of the subject. In FIGS. 5 and 6 both legs 117 of the subject are shown supported by the braces 110 slightly above the ankle (the legs are not being tested) and the braces serve as a leg rest to comfort the subject whether or not tests are being performed on an arm of the subject. In FIGS. 7-8, the brace 110 is shown in an elevated position wherein the pad 112 is disposed immediately behind the knee 118 so as to hold the leg in a fixed position as strength tests are being performed on a subject's leg or foot.

The additional apparatus and equipment to conduct the valuations of the subject may include a display 150 connected to the various load cells through a microprocessor 152. The load cells may be in the form of pressure gages, strain gages, or other known devices that will respond to the force applied against them and generate a signal that is a function of the force imposed. The display 150 may provide a single test report by expressing the strength as a raw score and/or a percent of a predicted normal. Alternatively, the display may graph disease progression over time and calculate the rate of disease progression based on percent of strength change expressed for example, per year.

In accordance with the present invention, it is contemplated that the limbs of the subject are tested one at a time. Because of the adjustability of each of the limb supports 16 and 18 and of the position of the seat 12, the arm support 16 is capable of serving effectively to immobilize, one at a time, both the left and right arm of the subject, and similarly the leg support 18 may be used one at a time with the left and right leg of the subject in the strength measurement of the leg and foot. The apparatus enables the use of a separate wheelchair or a fully adjustable specially designed chair for subjects depending upon their condition.

To insure that the limbs are disposed at the proper angle for each test being performed and so that repeated test results may be compared, in accordance with another aspect of the invention, goniometers 160 (see FIG. 7) are provided on each limb support to measure the angular disposition of each limb. These instruments may take many different forms and for convenience in this setting may reference the angle from the limbs themselves or from various portions of the limb supports.

The present invention greatly facilitates the measuring, testing and monitoring of maximal isometric muscle force in all four limbs and reduces the time required to perform these functions. Once seated in the equipment, the subject need not be moved from the seat until all of the procedures have been completed. The arms and legs are connected to the restraints one at a time and the load cells are positioned with respect to the limbs so as to respond to the forces exerted by the subject, and only after all of the procedures have been completed is the subject removed from the apparatus. The apparatus is not large and can conveniently be stored, and the cost of the apparatus is not prohibitive. The storage is further facilitated by the ability to collapse the limb supports about the base 10 and column 14. The apparatus when folded for storage as shown in FIG. 1 has a footprint approximately 3 ft.×3 ft., and when opened as in FIG. 2, approximately 3 ft.×6 ft.

While the apparatus has been described in terms of tests for measuring the loss of muscle strength as it relates to ALS patients, the apparatus has much broader applications including neurology, orthopedic and rehabilitation research and clinical practice, as well as for the fitness industry. Moreover, within the purview of the present invention the apparatus may permit the testing of many additional muscle groups including shoulder and hip flexion, extension, abduction adduction, etc.

Having thus described several aspects of several embodiments of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An isometric strength testing device comprising;
   a base for supporting a subject to be tested;
   a first limb support pivotally mounted to the base for alternatively engaging the right and left arms of a subject;
   a second limb support separate from the first limb support, the second limb support pivotally mounted to the base for alternatively engaging the right and left legs of a subject;
   a wrist brace associated with the first limb support for immobilizing the arm of a subject engaged by the first limb support;
   an ankle brace associated with the second limb support for immobilizing the arm of a subject engaged by the second limb support;
   load cells operatively connected to the braces for sensing the magnitude of the loads applied by the arms and legs of the subject to the supports; and
   a computer device for recording the loads sensed by the load cells.

2. The strength testing device as described in claim 1 wherein the first limb support includes an adjustable section for supporting the forearm of the subject in a substantially vertical position perpendicular to the upper arm,
   and a brace attached to the first limb support for holding the upper arm of the subject in a substantially horizontal position.

3. The strength testing device as described in claim 1 wherein the second limb support includes a leg brace for orienting the upper portion of the leg in a substantially horizontal position.

4. The strength testing device as described in claim 1, further comprising a column mounted on the base, wherein at least one of the first and second limb supports includes a sleeve movably mounted to the sleeve for vertical movement of the at least one of the first and second limb supports on the column.

5. Isometric strength testing apparatus comprising:
   a base;
   a chair assembly on the base for use by a subject to be tested;
   a column mounted on the base;

an adjustable support assembly mounted on the column for immobilizing a limb of a subject seated in the chair assembly, wherein the support assembly is mounted for vertical movement on the column;

a load cell associated with the support assembly for generating a signal that is a function of the force exerted by the subject against the load cell;

and a computer connected to the cell for displaying and/or recording the forces imposed by the subject.

6. The apparatus of claim 5 wherein the support assembly includes a plurality of sections hingedly connected end-to-end enabling the position of the support assembly to be altered for accommodating subjects of different size and for enabling either a left limb or a right limb to be immobilized while the subject remains in the chair assembly.

7. The apparatus of claim 5 wherein the support assembly may be raised or lowered on the column and is freely moved in a horizontal plane.

8. The apparatus of claim 5 wherein the chair assembly enables the chair to be raised, lowered, and to move toward and away with respect to the column for accommodating the subject.

9. The apparatus of claim 5, wherein the support assembly includes a sleeve movably mounted to the column for mounting the support assembly to the column.

10. The apparatus of claim 5, further comprising a second adjustable support assembly mounted on the column for immobilizing a limb of the subject seated in the chair assembly, wherein the second support assembly is mounted for vertical movement on the column.

11. Isometric strength testing apparatus comprising:
a base;
a chair assembly on the base for use by a subject to be tested;
a column mounted on the base;
a pair of adjustable support assemblies mounted on the column, one for immobilizing one at a time each leg of a subject seated in the chair assembly and the other for immobilizing one at a time each of the arms of a subject seated in the chair assembly;
load cells associated with each of a support assemblies for generating signal that is a function of the force exerted by the subject against the cells;
a computer connected to the cells for displaying and/or recording the forces imposed by the subject; and
wherein the chair assembly includes a platform that supports a chair which may be removed from the platform enabling the chair to be replaced by a detached chair or wheelchair.

12. The apparatus of claim 11 wherein the platform may be folded upwardly on the base to reduce the footprint size of the apparatus for storage.

13. The apparatus of claim 12 wherein the platform may be tilted independent of the folding action to tilt the chair toward and away from the column.

14. Isometric strength testing apparatus comprising:
a base;
a chair assembly on the base for use by a subject to be tested;
a column mounted on the base;
a pair of adjustable support assemblies mounted on the column, one for immobilizing one at a time each leg of a subject seated in the chair assembly and the other for immobilizing one at a time each of the arms of a subject seated in the chair assembly;
load cells associated with each of a support assemblies for generating a signal that is a function of the force exerted by the subject against the cells;
a computer connected to the cells for displaying and/or recording the forces imposed by the subject; and
wherein each of the support assemblies includes a sleeve movably mounted for vertical movement on the column and further include a plurality of sections pivoted end-to-end on the sleeve so that each may be raised and lowered for accommodating the subject's size and the particular limb to be tested.

15. The apparatus of claim 14 wherein both support assemblies may be positioned in close proximity to the column for storage.

16. A method of testing maximal isometric force of a subject comprising the steps of;
providing an adjustable apparatus that includes a support for the body of a subject to be tested and a single leg restraint and a single arm restraint,
positioning a subject on the support of the adjustable apparatus,
immobilizing one leg of the subject on the leg restraint and providing a load cell on that restraint to measure the force applied on it by the leg of the subject,
removing the one leg of the subject from the restraint and adjusting the same restraint and load cell for immobilizing the other leg of the subject on it and measuring the force applied on the load cell by the other leg of the subject,
immobilizing one arm of the subject on the arm restraint and providing a load cell on that restraint to measure the force applied on the load cell by that arm of the subject,
and removing the one arm of the subject from the restraint and adjusting the same arm restraint and load cell and immobilizing the other arm of the subject on it and measuring the force applied to the load cell by that arm of the subject 17. The method of claim 16 including the step of recording the measured forces.

18. Isometric strength testing apparatus comprising,
a base;
a chair assembly on the base for use by a subject to be tested;
a first column mounted vertically adjustable support assembly for immobilizing a first limb of a subject seated in the chair assembly;
a second column mounted vertically adjustable support assembly for immobilizing a second limb of a subject seated in the chair assembly;
load cells associated with each of the support assemblies for generating a signal that is a function of the force exerted by the subject against the cells; and
a computer in communication with the cells for displaying and/or recording the forces imposed on the cells.

19. The apparatus of claim 18, wherein the chair assembly enables the chair to be raised and lowered for accommodating the subject.

* * * * *